(12) United States Patent
Zhang et al.

(10) Patent No.: US 9,493,424 B2
(45) Date of Patent: Nov. 15, 2016

(54) ANTIFUNGAL COMPOUND

(71) Applicant: Agency for Science, Technology and Research, Singapore (SG)

(72) Inventors: Yugen Zhang, Singapore (SG); Jackie Y. Ying, Singapore (SG); Lihong Liu, Singapore (SG); Hong Wu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/420,859

(22) PCT Filed: Aug. 7, 2013

(86) PCT No.: PCT/SG2013/000333
§ 371 (c)(1),
(2) Date: Feb. 10, 2015

(87) PCT Pub. No.: WO2014/025314
PCT Pub. Date: Feb. 13, 2014

(65) Prior Publication Data
US 2015/0203454 A1    Jul. 23, 2015

(30) Foreign Application Priority Data
Aug. 10, 2012   (SG) .................................. 201205952

(51) Int. Cl.
*A61K 31/787*   (2006.01)
*C07D 233/61*   (2006.01)
*A01N 43/50*    (2006.01)

(52) U.S. Cl.
CPC ............. *C07D 233/61* (2013.01); *A01N 43/50* (2013.01); *A61K 31/787* (2013.01)

(58) Field of Classification Search
None
See application file for complete search history.

(56) References Cited

U.S. PATENT DOCUMENTS

2006/0024264 A1    2/2006   Kuroda et al.

FOREIGN PATENT DOCUMENTS

| | | |
|---|---|---|
| JP | H04-202305 | 7/1992 |
| WO | WO-2012/050531 | 4/2012 |
| WO | WO-2014/025314 | 2/2014 |

OTHER PUBLICATIONS

"International Application No. PCT/SG2013/000333, International Search Report and Written Opinion mailed Oct. 14, 2013", 9 pgs.

*Primary Examiner* — Samantha Shterengarts
(74) *Attorney, Agent, or Firm* — Schwegman Lundberg & Woessner, P.A.

(57) ABSTRACT

There is provided compound for use in therapy, the compound comprising repeating units of hydrophilic heterocyclic amine monomers that are coupled by hydrophobic linkers selected to confer a therapeutic effect. There is also provided the use of the above compound in the manufacture of a medicament for the treatment of a fungal infection and a method of treating a fungal infection using the above compound.

14 Claims, 11 Drawing Sheets

ANTIFUNGAL COMPOUND

PRIORITY CLAIM TO RELATED APPLICATIONS

This application is a U.S. national stage application filed under 35 U.S.C. §371 from International Application Serial No. PCT/2013/000333, which was filed Aug. 7, 2013, and published as WO 2014/025314 on Feb. 13, 2014, and which claims priority to Singapore Application No. 201205952-3, filed Aug. 10, 2012, which applications and publication are incorporated by reference as if reproduced herein and made a part hereof in their entirety, and the benefit of priority of each of which is claimed herein.

TECHNICAL FIELD

The present invention generally relates to an antifungal compound. The present invention also relates to the use of the antifungal compound and methods of treating a fungal infection using the antifungal compound.

BACKGROUND

Keratitis is one of the leading global causes of ocular morbidity, and it is also an eye disease that may lead to blindness. One source of keratitis may be attributed to fungi infection of the eye. These fungi may include yeast-like fungi such as *Candida albicans* (*C. albicans*) or filamentous fungi such as *Aspergillus fumigatus* and *Aspergillus niger* (*A. niger*).

Conventional therapies mainly involve the use of clinical antifungal or antimicrobial drugs which often fall short of their effectiveness due to various reasons.

Fungal keratitis infection often exists as a biofilm, which is particularly difficult to clear because of its encasement in a protective and impermeable extracellular matrix. Therefore, a much higher dosage of antimicrobials is needed for fungi biofilm clearance as compared to planktonic microbial substrates.

Another reason for the ineffectiveness of conventional therapies is due to the shortage of broad-spectrum efficient antifungal drugs. Current clinical drugs for treating fungal keratitis may comprise either azole compounds or polyenes. Examples may include fluconazole and amphotericin B respectively as shown below.

The fungistatic nature of azole compounds, which function via enzyme inhibition, requires a prolonged course of application. Moreover, azoles are extremely unstable such that their topical solutions must be stored at low temperatures and protected from light.

On the other hand, polyenes, which function via disrupting the permeability of ions through the cell membrane, are expensive.

Notably, the above clinical drugs exhibit poor penetration, solubility and stability which limit their application for fungal keratitis treatment. These limitations, together with the development of drug resistance, have further led to the low efficacy and unsatisfactory outcome associated with the current therapies for fungal keratitis.

To mitigate the above limitations and the growing health threat posed by resistant pathogenic microorganisms, further developments of antibiotics with new mechanisms of action, including peptides and synthetic polymers, have attracted considerable research interests. Amphiphilic peptides (AMP) or synthetic polymers have unique killing mechanism that may slow down the development of drug resistance. However, no antifungal properties have been observed for these new materials.

A more recent development includes the use of imidazolium salts (IMSs) as clinical drugs. However, these biocidal IMSs usually have very low selectivity, minimal hemolytic concentration (represented as MHC or MIC), usually in the range of 1.25-5, which excludes them from their potential systemic usage.

Accordingly, there is a need to provide an antifungal drug that overcomes, or at least ameliorates, one or more of the disadvantages described above.

There is also a need to provide an effective therapy for the treatment of keratitis that overcomes, or at least ameliorates, one or more of the disadvantages described above.

SUMMARY

According to a first aspect, there is provided a compound for use in therapy, the compound comprising repeating units of hydrophilic heterocyclic amine monomers that are coupled by hydrophobic linkers selected to confer a therapeutic effect.

Advantageously, the compound may have a biocidal activity and may be used as a fungicide. The compound may

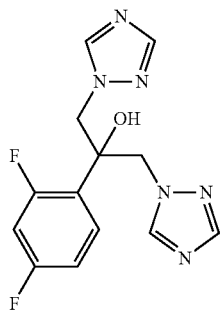

Fluconazole

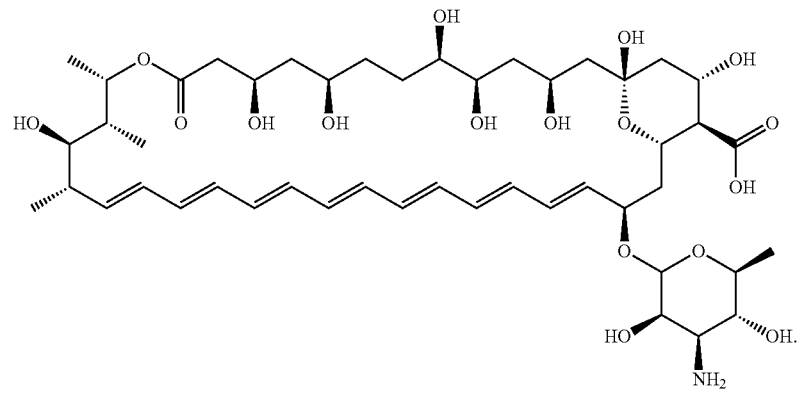

Amphotericin B kill a fungus by making the cell membrane of the fungus porous, leading to leakage of the cytoplasm or by interfering with cell wall biosynthesis. The compound may have a lower minimal inhibition concentration as compared to other conventional antifungal compounds.

The compound may be used against planktonic fungi as well as on fungi biofilm. The compound may have a high potency against a fungus even at a low minimal inhibition concentration.

When the compound is used on a fungi biofilm, the compound may be able to penetrate through the biofilm to thereby inhibit the growth of the biofilm and kill adhered fungi in the biofilm. The effective concentration required to kill the adhered fungi may be substantially lower as compared to conventional antifungal compounds such as amphotericin B or fluconazole.

Advantageously, the compound may potentially escape the mechanisms involved in multidrug resistance and be able to exert its antifungal effects on a fungus.

Advantageously, the compound may have a significantly improved selectivity against a fungus as compared to simple (that is, non-polymeric) imidazolium salts.

Advantageously, the compound may be chemically stable when stored for a period of time, without requiring protection from light.

Advantageously, the compound may be biocompatible and may not be toxic to a patient.

The compound may be easy to manufacture.

According to a second aspect, there is provided a compound for use in treating a fungal infection, the compound comprising repeating units of hydrophilic heterocyclic amine monomers that are coupled by hydrophobic linkers selected to confer an antifungal effect.

According to a third aspect, there is provided use of a compound in the manufacture of a medicament for the treatment or prevention of a fungal infection, the compound comprising repeating units of hydrophilic heterocyclic amine monomers that are coupled by hydrophobic linkers selected to confer an antifungal effect.

According to a fourth aspect, there is provided a method of treating or preventing a fungal infection comprising the step of administering an antifungal amount of a compound to a patient, in need thereof, the compound comprising repeating units of hydrophilic heterocyclic amine monomers that are coupled by hydrophobic linkers selected to confer an antifungal effect.

According to a fifth aspect, there is provided a method of reducing the fungal cell count on a fungal biofilm, comprising the step of administering an effective fungicidal amount of a compound comprising repeating units of hydrophilic heterocyclic amine monomers that are coupled by hydrophobic linkers selected to confer the fungicidal effect.

According to a sixth aspect, there is provided a compound selected from:

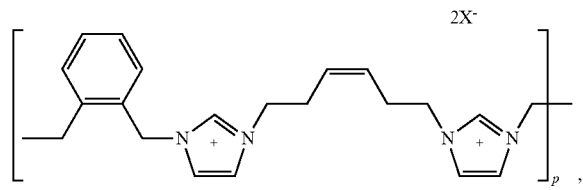

Formula (III)

wherein p is 6 to 20, and $X^-$ is a counterion.

According to a seventh aspect, there is provided a stable pharmaceutical formulation comprising a compound comprising repeating units of hydrophilic heterocyclic amine monomers that are coupled by hydrophobic linkers selected to confer a therapeutic effect in a pharmaceutically acceptable buffer.

DEFINITIONS

The following words and terms used herein shall have the meaning indicated:

The term "alkyl" refers to monovalent straight chain or branched chain saturated aliphatic groups having from 1 to 6 carbon atoms, eg, 1, 2, 3, 4, 5 or 6 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl and the like. Alkyl groups may be optionally substituted. alkenyl or alkynyl The term "alkenyl" refers to divalent straight chain or branched chain unsaturated aliphatic groups containing at least one carbon-carbon double bond and having from 2 to 6 carbon atoms, e.g., 2, 3, 4, 5 or 6 carbon atoms. For example, the term alkenyl includes, but is not limited to, ethenyl, propenyl, butenyl, 1-butenyl, 2-butenyl, 2-methylpropenyl, 1-pentenyl, 2-pentenyl, 2-methylbut-1-enyl, 3-methylbut-1-enyl, 2-methylbut-2-enyl, 1-hexenyl, 2-hexenyl, 3-hexenyl, 2,2-dimethyl-2-butenyl, 2-methyl-2-hexenyl, 3-methyl-1-pentenyl, 1,5-hexadienyl and the like. Alkenyl groups may be optionally substituted.

The term "alknlyl" refers to trivalent straight chain or branched chain unsaturated aliphatic groups containing at least one carbon-carbon triple bond and having from 2 to 6 carbon atoms, eg, 2, 3, 4, 5 or 6 carbon atoms. For example, the term alkynyl includes, but is not limited to, ethynyl, propynyl, 1-butynyl, 2-butynyl, 1-pentynyl, 2-pentynyl, 1-hexynyl, 2-hexynyl, 3-hexynyl, 3-methyl-1-pentynyl, and the like. Alknlyl groups may be optionally substituted.

The term "aryl", or variants such as "aromatic group" or "arylene" as used herein refers to monovalent ("aryl") and divalent ("arylene") single, polynuclear, conjugated and fused residues of aromatic hydrocarbons having from 6 to 10 carbon atoms. Such groups include, for example, phenyl, biphenyl, naphthyl, phenanthrenyl, and the like. Aryl groups may be optionally substituted.

The term "cycloalkyl", refers to any stable 3, 4, 5, or 6-membered monocyclic or bicyclic, which may be saturated or partially unsaturated. Examples of such cycloalkyl groups include, but are not limited to, cyclopropyl, cyclobutyl, cyclopentyl or cyclohexyl. Cycloalkyls may be optionally substituted.

The term "halogen", or variants such as "halide" or "halo" as used herein, includes within its meaning fluorine, chlorine, bromine and iodine.

The term "substituted" as used herein means the group to which this term refers is substituted with one or more groups other than hydrogen provided that the indicated atom's normal valency is not exceeded, and that the substitution results in a stable compound. For example, substituent groups may be an alkyl, alkenyl or alkynyl.

The term "optionally substituted" as used herein means the group to which this term refers may be unsubstituted, or may be substituted with one or more groups other than hydrogen provided that the indicated atom's normal valency is not exceeded, and that the substitution results in a stable compound. For example, substituent groups may be an alkyl, alkenyl or alkynyl.

Any carbon or heteroatom with unsatisfied valences in the text, schemes, examples, structural formulae, and any Tables herein is assumed to have the hydrogen atom or atoms to satisfy the valences.

When compounded chemical names, e.g. "arylalkyl" and "alkylarylalkyl" are used herein, they are understood to have a specific connectivity to an imidazolium ring. The group listed farthest to the right (e.g. alkyl in "arylalkyl"), is the group that is directly connected to the imidazolium ring. Thus, an "arylalkyl" group, for example, is an alkyl group substituted with an aryl group (e.g. phenylmethyl (i.e., benzyl)) and the alkyl group is attached to the imidazolium ring. An "alkylaryl" group is an aryl group substituted with an alkyl group (e.g., p-methylphenyl (i.e., p-tolyl)) and the aryl group is attached to the imidazolium ring. Where this compounded group is connected between a pair of imidazolium rings, the outermost groups are the ones that are directly connected to the imidazolium rings. For example, in an "alkylarylalkyl" group such as methylphenylmethyl, each of the alkyl groups is respectively attached to each The term "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage.

The term "biofilm" is defined as an aggregate, association or accumulation of microorganisms and their extracellular products to form a structured community usually on a surface. This term includes biofilms at some distance away from a surface and which exist in multiple as well as single layers of cells.

The term "prodrug" is intended to include an inactive form of a compound which is transformed in vivo to the active form. Suitable prodrugs include esters, phosphonate esters etc, of the active form of the compound.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a compound will now be disclosed.

The compound may comprise repeating units of hydrophilic heterocyclic amine monomers that are coupled by hydrophobic linkers selected to confer a therapeutic effect.

The repeating units of the hydrophilic heterocyclic amine monomers and hydrophobic linkers may confer the antimicrobial property (such as antifungal property) to the compound.

The compound may have the general formula (I):

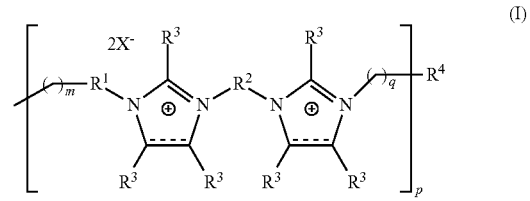

wherein:

$R^1$ and $R^2$ are independently selected from aryl, arylalkyl, alkylarylalkyl, alkylaryl, alkyl, cycloalkyl, alkenyl or alkynyl, said aryl, alkylaryl, alkylarylalkyl or alkylaryl being optionally substituted by alkyl, alkenyl or alkynyl;

each $R^3$ is independently selected from hydrogen, alkyl, alkenyl, alkynyl, aryl, cycloalkyl, heteroaryl, or heterocyclyl;

$R^4$ is selected from hydrogen or aryl, said aryl being optionally substituted by alkyl, alkenyl or alkynyl;

⁓⁓⁓⁓ is either a single bond or a double bond;

q is an integer selected from 0 to 3;

m is an integer selected from 0 to 3;

p is an integer selected from 2 to 50; and $X^-$ is a counterion.

In the compound of general formula (I), $R^1$ or $R^2$ confer the hydrophobic property to the compound.

In the compound of general formula (I), $R^1$ may be selected from aryl, alkylaryl or alkylarylalkyl. $R^1$ may be aryl selected from phenyl. $R^1$ may be arylalkyl selected from aryl$C_{1-6}$, such as phenylmethyl, phenylethyl, phenylpropyl, phenylbutyl, phenylpentyl or phenylhexyl. $R^1$ may be alkylarylalkyl selected from $C_{1-6}$aryl$C_{1-6}$, such as methylphenylmethyl, methylphenylethyl, methylphenylpropyyl, methylphenylbutyl, methylphenylpentyl, methylphenylhexyl, ethylphenylmethyl, ethylphenylethyl, ethylphenylpropyyl, ethylphenylbutyl, ethylphenylpentyl, ethylphenylhexyl, propylphenylmethyl, propylphenylethyl, propylphenylpropyyl, propylphenylbutyl, propylphenylpentyl, propylphenylhexyl, butylphenylmethyl, butylphenylethyl, butylphenylpropyyl, butylphenylbutyl, butylphenylpentyl, butylphenylhexyl, pentylphenylmethyl, pentylphenylethyl, pentylphenylpropyyl, pentylphenylbutyl, pentylphenylpentyl, pentylphenylhexyl, hexylphenylmethyl, hexylphenylethyl, hexylphenylpropyyl, hexylphenylbutyl, hexylphenylpentyl or hexylphenylhexyl. Where $R^1$ is an aryl, arylalkyl or alkylarylalkyl, the aryl, arylalkyl or alkylarylalkyl may be substituted at the ortho position or at the meta position. Hence, where $R^1$ is phenyl, phenylmethyl or methylphenylmethyl, the phenyl, phenylmethyl or methylphenylmethyl may be substituted at the ortho position or at the meta position.

In the compound of general formula (I), $R^2$ may be selected from aryl, alkylaryl or alkylarylalkyl. $R^2$ may be aryl selected from phenyl. $R^2$ may be arylalkyl selected from aryl$C_{1-6}$, such as phenylmethyl, phenylethyl, phenylpropyl, phenylbutyl, phenylpentyl or phenylhexyl. $R^2$ may be alkylarylalkyl selected from $C_{1-6}$aryl$C_{1-6}$, such as methylphenylmethyl, methylphenylethyl, methylphenylpropyyl, methylphenylbutyl, methylphenylpentyl, methylphenylhexyl, ethylphenylmethyl, ethylphenylethyl, ethylphenylpropyyl, ethylphenylbutyl, ethylphenylpentyl, ethylphenylhexyl, propylphenylmethyl, propylphenylethyl, propylphenylpropyyl, propylphenylbutyl, propylphenylpentyl, propylphenylhexyl, butylphenylmethyl, butylphenylethyl, butylphenylpropyyl, butylphenylbutyl, butylphenylpentyl, butylphenylhexyl, pentylphenylmethyl, pentylphenylethyl, pentylphenylpropyyl, pentylphenylbutyl, pentylphenylpentyl, pentylphenylhexyl, hexylphenylmethyl, hexylphenylethyl, hexylphenylpropyyl, hexylphenylbutyl, hexylphenylpentyl or hexylphenylhexyl. Where $R^2$ is an aryl, arylalkyl or alkylarylalkyl, the aryl, arylalkyl or alkylarylalkyl may be substituted at the ortho position or at the meta position. Hence, where $R^2$ is phenyl, phenylmethyl or methylphenylmethyl, the phenyl, phenylmethyl or methylphenylmethyl may be substituted at the ortho position or at the meta position.

$R^2$ may be an alkyl or an alkenyl group. $R^2$ may be $C_{1-6}$-alkyl or $C_{2-6}$-alkenyl. $R^2$ may be selected from the group consisting of methyl, ethyl, propyl, butyl, pentyl, hexyl, ethylene, propylene, butylene, pentylene or hexylene. The hexylene may be 3-hexenyl.

Due to the presence of short carbon chains in the groups $R^1$ or $R^2$ (for example $C_{1-6}$-alkyl, $C_{2-6}$-alkenyl, aryl, aryl-$C_{1-6}$-alkyl, $C_{1-6}$-alkyl-aryl-$C_{1-6}$-alkyl, $C_{1-6}$-alkylaryl, $C_{3-6}$-cycloalkyl or $C_{2-6}$-alkynyl), the use of strongly hydrophobic long alkyl chains (for example, alkyls having more than 10 carbon atoms) as the hydrophobic linker is avoided. By avoiding the use of strongly hydrophobic long alkyl chains, the compound may have a higher selectivity and/or lower minimal inhibition concentration.

In the compound of general formula (I), $R^3$ may be hydrogen.

In the compound of general formula (I), $R^4$ may be hydrogen or aryl such as phenyl.

In the compound of general formula (I), X may be a halide selected from the group consisting of fluoride, iodide, bromide and chloride.

The compound of formula (I) may have a molecular weight in the range of about 1000 to about 3000, about 1000 to about 2000, about 1300 to about 1400, about 2000 to about 3000, about 2500 to about 3000 or about 2700 to about 2800. The molecular weight of the compound may be about 1300 or about 2700.

The compound of formula (I) may be selected from formula (II) or formula (III):

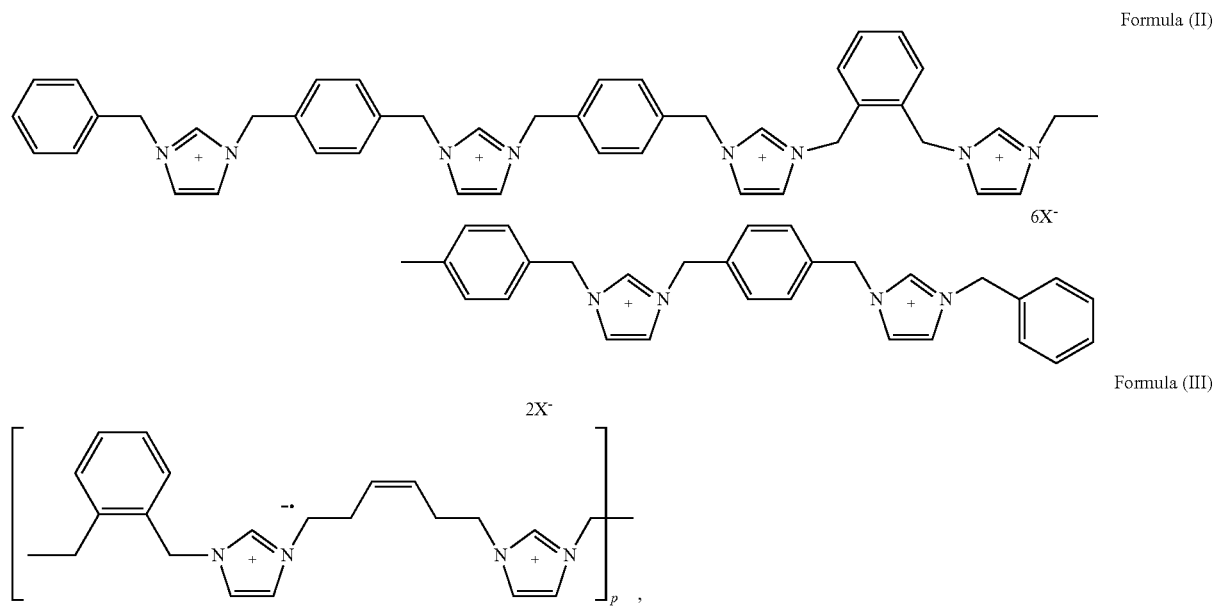

Formula (II)

Formula (III)

wherein p is 6 to 20.

Where the compound of formula (I) is the compound of formula (II), this compound is an oligomer with 6 imidazolium units in the structure ($C_{72}H_{72}N_{12}Cl_6$) having a molecular weight of 1316. This compound is termed as "IBN-1" in the following examples.

Where the compound of formula (I) is the compound of formula (III), this compound is a polymer with an average molecular weight of 2781 by gel permeation chromatography (GPC) (Mw/Mn=1.03). This compound is termed as "PIM-45" in the following examples.

The inventors have found that by having the imidazole linked with a hydrophobic linker to form an imidazolium polymer (or oligomer), this polymer (or oligomer) exhibits antifungal effects, as compared to a simple imidazolium salt (monomer) which does not have any antifungal activity (in which the minimal inhibition concentration has been found to be more than 1000 ppm) or antibacterial activity.

The compound of formula (I) may be used in therapy. The compound may have potent biocidal activities, whilst at the same time, possess limited or negligible hemolytic effects. Due to the limited or negligible hemolytic effects of the compound, this means that the $HC_{50}$ concentration (which is the concentration of the compound required to kill 50% of a given concentration of red blood cells) of the compound is at least 10 times higher than its minimum inhibitory concentration (MIC) with respect to a defined fungus. In another embodiment, the $HC_{50}$ concentration of the compound is at least 15 times that its MIC value. In yet another embodiment, the $HC_{50}$ concentration of the polymer is at least 25 times that of its MIC value. In general, the higher the multiple of $HC_{50}$ relative to its MIC value, the safer the compound is for administration to a living organism. The compound may have an improved selectivity for a selected fungi as compared to simple imidazolium salts. The compound may be biocompatible and may not be toxic to a patient.

The compound may be used to treat a fungal infection. The fungal infection may be caused by a fungi selected from the genus group consisting of *Candida, Aspergillus, Cryptocccus, Histoplasma, Pneumocystis, Fusarium* and *Stachybotrys*. The fungi may be selected from the group consisting of *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Fusarium solani Fusarium oxysporum, Fusarium verticillioides, Fusarium proliferatum Stachybotrys chartarum), Aspergillus niger*. The fungi may be *Candida albicans* or the fungi may be *Aspergillus niger*.

The fungi maybe present as a biofilm and hence the compound may be used to reduce or kill the fungi that are present in the biofilm. The compound may be able to penetrate the biofilm in order to effectively kill or reduce the fungal cell count in the biofilm. The MIC of the compound in killing biofilm-grown fungi cells may be at least 2 times, at least 3 times, at least 4 times or at least 5 times lower as compared to conventional antifungal compounds such as amphotericin B or fluconazole.

The fungal infection may be selected from the group consisting of keratitis, candidiasis, aspergillosis, cryptococcosis and onychomycosis. The fungal infection may be selected from the group consisting of fungal keratitis, angular cheilitis, antibiotic candidiasis, candidal intertrigo, candidal paronychia, candidal vulvovaginitis, candidid, chronic mucocutaneous candidiasis, congenital cutaneous candidiasis, diaper candidiasis, erosio interdigitalis blastomycetica, oral candidiasis, perianal candidiasis, systemic candidiasis, allergic bronchopulmonary aspergillosis, pulmonary aspergilloma, invasive aspergillosis, wound or cutaneous cryptococcosis, pulmonary cryptococcosis, cryptococcal meningitis, distal subungual onychomycosis, white superficial onychomycosis, proximal subungual onychomycosis and candidal onychomycosis.

In treating the fungal infection, the compound may have minimum inhibition concentration in the range of about 10 to about 130 ppm, about 10 to about 20 ppm, about 30 to about 40 ppm, about 60 to about 70 ppm, about 100 to about 130 ppm or about 120 to about 130 ppm.

There is also provided the use of a compound in the manufacture of a medicament for the treatment or prevention of a fungal infection, said compound comprising repeating units of hydrophilic heterocyclic amine monomers that are coupled by hydrophobic linkers selected to confer an antifungal effect. The compound may have the general formula (I) as mentioned above.

There is also provided a method of treating or preventing a fungal infection comprising the step of administering an antifungal amount of a compound to a patient in need thereof, the compound comprising repeating units of hydrophilic heterocyclic amine monomers that are coupled by hydrophobic linkers selected to confer an antifungal effect. The compound may have the general formula (I) as mentioned above.

There is also provided a method of reducing the fungal cell count on a fungal biofilm, comprising the step of administering an effective fungicidal amount of a compound comprising repeating units of hydrophilic heterocyclic amine monomers that are coupled by hydrophobic linkers selected to confer the fungicidal effect. The compound may have the general formula (I) as mentioned above.

There is also provided a compound having the general formula (III):

Formula (III)

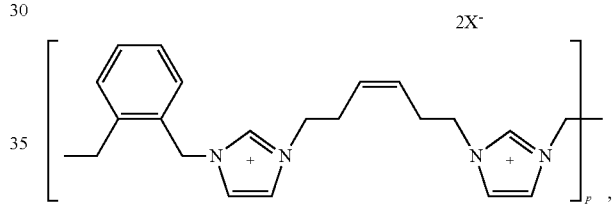

wherein p is 6 to 20, and $X^-$ is a counterion.

There is also provided a stable pharmaceutical formulation comprising a compound comprising repeating units of hydrophilic heterocyclic amine monomers that are coupled by hydrophobic linkers selected to confer a therapeutic effect in a pharmaceutically acceptable buffer. The compound may have the general formula (I) as mentioned above. The pharmaceutically acceptable buffer is not particularly limited and may be phosphate buffered saline. The compound may be stable for a long period of time as compared to conventional antifungal compounds such as amphotericin B or fluconazole. The compound may not require the use of special protective containers in order to protect against degradation by light as compared to conventional antifungal compounds. The pharmaceutical formulation may be kept for a minimum of 6 months without chemical degradation of the compound or loss in the fungicidal activities of the compound. The pharmaceutical formulation may be a topical formulation that can be kept for a long period of time for routine use.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Figure 1A:
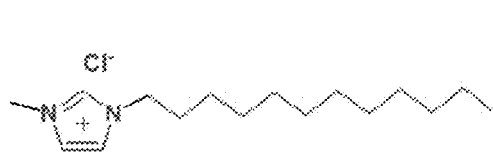
FIG. 1a depicts a structural example of typical biocide imidazolium salt.
Figure 1B:
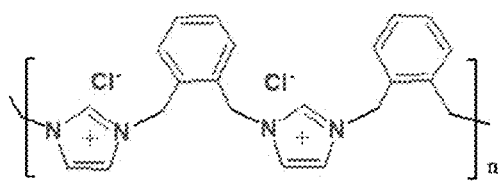
FIG. 1b depicts a structural example polyimidazolium salts (PIMS).

Non-limiting examples of the invention and a comparative example will be further described in greater detail by reference to specific Examples, which should not be construed as in any way limiting the scope of the invention.

Materials and Methods

Synthesis of PIMSs

IBN-1 and PIM-45 were synthesized based on condensation reactions as indicated in examples 1 and 2 below. All solvents were of HPLC grade, and purchased from Aldrich or Fluka. All starting materials were commercially available and used as received, unless otherwise indicated. Nuclear magnetic resonance (NMR) spectra were obtained using a Brucker AV-400 (400 MHz) spectrometer. Chemical shifts were reported in ppm from tetramethylsilane with the solvent resonance as the internal standard.

Antifungal Studies

*Candida albicans* (American Type Culture Collection (ATCC) 10231, yeast) and *Aspergillus niger* were used as representative fungi for testing the antimicrobial functions of the compounds. *C. albicans* suspensions were prepared from fresh overnight cultures in Yeast Mold (YM) (Difco) broth using −80° C. frozen stock cultures. Subsamples of these cultures were grown for another 3 hours, and adjusted to an optical density of about 0.1 at 600 nm, giving a density of $10^7$-$10^8$ CFU/mL. *A. niger* were cultured on Sabouraud dextrose agar plates in incubator at 37° C. The spores were harvested from 96 hours cultures and suspended homogeneously in phosphate buffer saline (PBS). A homogeneous spore suspension was obtained by incubating the tube at 37° C. for 60 minutes with intermittent shaking. The spores in the suspension were counted and their number was adjusted to $1 \times 10^8$ spores/ml before performing the experiments. Amphotericin B (obtained from Sigma-Aldrich, sterilized in deionized (DI) water and fluconazole (obtained from Ningjiang Pharmaceutical & Chemical Corp., China) were examined as the commercial antifungal agents.

The MICS of fungicidal agents were determined by microdilution assay. For *C. albicans*, the yeast inoculum used was 100 μL/well for fungicidal agents ($10^7$-$10^8$ CFU/mL) in 2-fold dilutions, producing concentrations of 1-250 μg/mL in the media and giving a total amount of 200 μL/well. The 96-well microtiter plates (Nunc Microwell Plates) were incubated at 22° C. for 24 hours. MIC corresponded to the minimum concentration necessary to inhibit complete cell growth. For *A. niger*, autoclaved sabouraud dextrose broth (90 μL) was added to the wells of culture plates. Various concentrations of PIM-45 and IBN-1 in the range of 1000 ppm were prepared in the wells by 2-fold dilution method, and these wells were inoculated with 10 μL of spore suspension containing $1\times10^6$ spores. The plates were incubated at 37° C. and examined macroscopically after 24 hours for the growth of *A. niger*. Appropriate control wells without any treatment were included in the study. PIM-45 and IBN-1 were considered to be active if the wells appeared clear without any visible growth of *A. niger* and the results were expressed as MIC. The assay was performed in four replicates for each concentration.

Electron Microscopy Studies

A 1.5-mL suspension of *C. albicans* was incubated with 0.5 mL of PIM-45 at a concentration of 2× or 10×MIC for 8 hours. The control was prepared from the same batch of bacterial suspension as the treated samples. The mixture was centrifuged at 4000 rpm for 5 min, and washed with PBS (pH 7.4) thrice. The fungi pellet was fixed in 2.50 glutaraldehyde in PBS overnight at 4° C., followed by centrifugation and washing with PBS twice and with DI water thrice for 10 minutes. The post-fixation with 1% $OsO_4$ was performed in PBS (pH 7.0) for 1 hour. The fixed sample was then dehydrated in ethanol solutions of a graded series of concentrations. The sample was infiltrated with mixtures of acetone and Spurr resin (volume ratio=1:1 to 1:3) at room temperature for 1 hour and 3 hours, respectively. The pellet was finally embedded in pure Spurr resin overnight. Ultrathin sections of about 80 nm were obtained using a Reichert-Jung Ultracut ultramicrotome, mounted on formvar/carbon-coated 200-mesh copper grids, and post-stained with uranyl acetate and lead citrate for 15 minutes each prior to transmission electron microscopy (TEM) studies (JEM-1230, JEOL, Japan) at an acceleration voltage of 80 keV.

The morphologies of *A. niger* cells treated with IBN-1 were observed using a field emission scanning electron microscopy (FESEM) (JEOL JSM-7400F) operated at an accelerating voltage of 4.0-6.0 keV. The microorganisms grown in a pure broth or incubated with IBN-1 were harvested by centrifugation at 4000 rpm for 5 minutes. They were washed with PBS thrice, and then fixed overnight in PBS containing 2.5% of glutaraldehyde. The cells were further washed with DI water, followed by dehydration using a series of ethanol washes. Several drops of the suspension were placed on a holey formvar/carbon-coated 200-mesh copper grid, and left to dry under room temperature. The samples were coated with platinum prior to SEM analyses.

Soft Contact Lens and Biofilm Formation

Lotrafilcon A contact lenses used in the present study were purchased from CIBA Vision with a power of +1.50 diopters. The contact lenses were washed with PBS and immersed in YM broth overnight before they were punched into smaller pieces of 2 mm in diameter. To grow *C. albicans* biofilms, the lenses were placed in 6-well tissue culture plates with 4 mL of yeast suspension ($10^7$ CFU/mL) and incubated for 3 hours at 22° C. The contact lenses were gently washed with PBS to remove non-adherent yeast cells and immersed in YM broth for 48 hours at 22° C. with shaking at 100 rpm. Biofilms were quantified using direct plate counting. The yeast cells on contact lens were detached and dispersed in PBS by ultrasonication for 3 minutes. After making 10-fold dilutions, 20-μL sampling aliquots were plated on solid Lysogeny broth (LB) plate and incubated at 22° C. for 48 hours before the colony number was counted for determination of surviving CFU. Data from triplicate plate counts were averaged.

Biofilm Susceptibility (In Vitro Keratitis Model Treatment)

The *C. albicans* biofilms supported on contact lenses were transferred to fungicidal agent-containing PBS, and incubated at 22° C. for 24 hours. The biofilms were ultrasonicated for 3 minutes, and then serially diluted in PBS. The viable yeast cells were enumerated as described above.

Cytotoxicity and In Vivo Acute Toxicity Evaluation

Human primary corneal epithelial (HCEP) cells were purchased from (CELLnTEC, Switzerland) and cultivated using CnT-20 medium (CELLnTEC, Switzerland) with 5% $CO_2$ and humidified atmosphere. The medium was changed every 2 days. The effects of materials on HCEP cell viability was examined using 3-(4,5-dimethylthiazol-2-yl)-5-(3-carboxy-methoxyphenyl)-2-(4-sulfophenyl)-2H-tetrazolium (MTS) assay. Cells were seeded in 24-well plates in 1 mL of CnT-20 medium. Cells were allowed to attach and then treated with different concentrations of PIM-45 and IBN-1. 200 μL of MTS solution was added 12 hours after treatment. After 3 hours of incubation at 37° C. in 5% $CO_2$, the light absorbance was measured at 490 nm with a microplate reader. The cell viability was expressed as the ratio of the number of viable cells with treatment to that without treatment. Experiments were repeated in triplicates, and consistent results were obtained.

Source of Mice 8-week-old adult C57BL/6 mice (18-22 g) were used for animal studies. All mice eyes were examined for absence of ocular pathology before experiments were initiated. The experimental protocol was approved by the Institutional Animal Care and Use Committee of Biological Resource Centre, Agency for Science, Technology and Research (A*STAR), Singapore.

Contact Lens-Associated Keratitis Model

The black mouse keratitis model was established by employing contact lens biofilm infection, which is described as follows. The mice were anesthetized by ketamine (150 mg/kg) and xylazine (10 mg/mL) via intraperitoneal injection (I.P.). Additional topical anesthetic in the form of 0.5% tetracaine hydrochloride eye drops (Bausch & Lomb, Tampa, Fla.) was also administered.

A total of 45 mice were used in this study. A 1-mm filter paper disc moistened with 99% 1-heptanol (Sigma-Aldrich, Lausanne, Switzerland) was placed on the center of the cornea for 40 seconds. The corneal epithelium was traumatically wiped out and the eyes were rinsed with PBS to remove any remaining traces of 1-heptanol. A 2 mm-diameter punch from the contact lense with *C. albicans* biofilm was then placed on the denuded cornea surface. The contact lenses were kept inside the eyes by closing the eye lids with silk sutures. The *C. albicans* cells were grown on the eyeball 18 hours after inoculation; eye ulcer with a leathery, tough, raised surface was observed. A disease grading from 0 (no disease) to 4 (severe disease) was established for evaluating treatment efficacy (see Table 1 below). The mice were immune suppressed by subcutaneous injection of cyclophosphamide (Sigma-Aldrich, 180 g/kg).

TABLE 1

Clinical grading and scoring for in vivo keratitis treatment

| | Disease score | | | | |
|---|---|---|---|---|---|
| | 0 | 1 | 2 | 3 | 4 |
| Clinical description | Clear cornea | Slightly cloudy cornea | Cloudy cornea; iris and pupil are visible | Cloudy cornea; opacity not yet uniform | Nearly uniform opacity of cornea |
| % opacity | 0 | 1-25 | 26-50 | 51-75 | 76-95 |
| Degree of disease | No disease | Mild | Moderate | Moderate to severe | Severe |

Example 1

Synthesis of IBN-1

Figure 2:
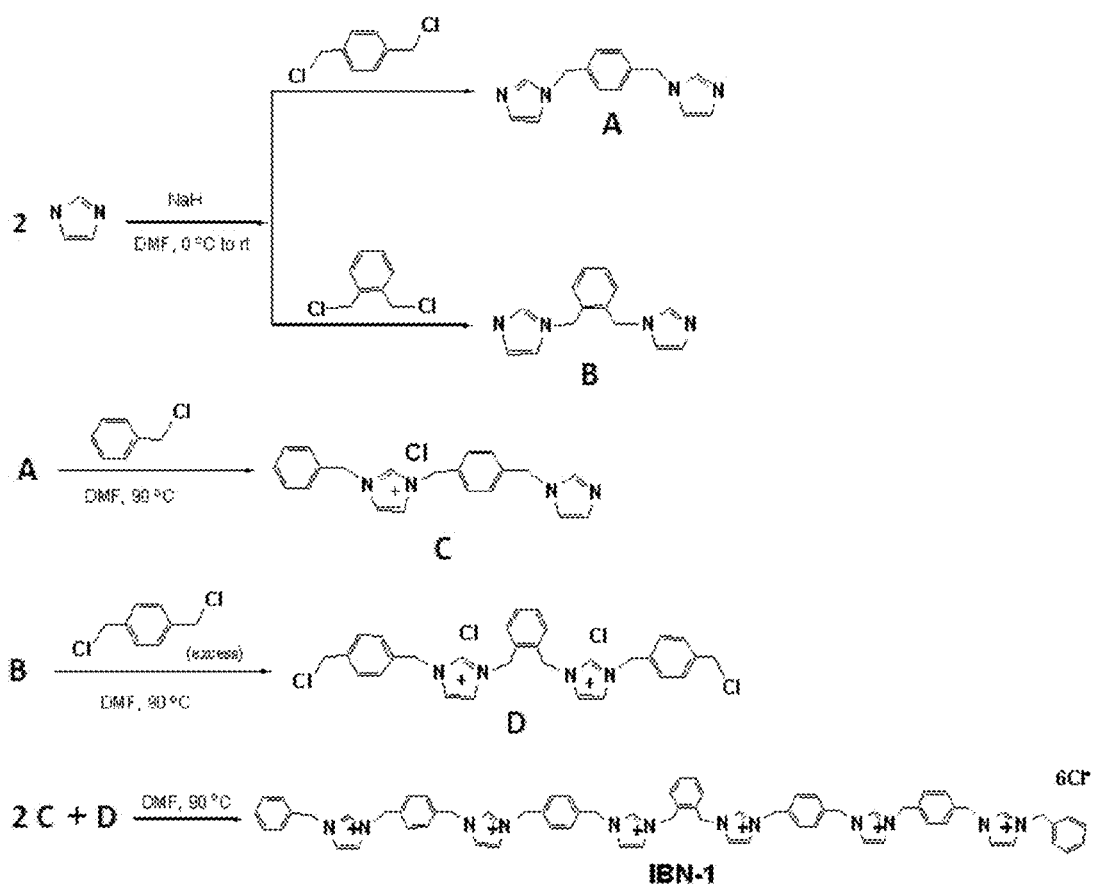
FIG. 2 depicts a schematic diagram for the synthesis of IBN-1.

FIG. 2 illustrates the synthesis of IBN-1.

For A, NaH (60% in oil, 440 mg, 11 mmol) was added to a N,N'-dimethylformamide (DMF) solution of imidazole (680 mg, 10 mmol), and the resulting suspension was stirred at room temperature for 2 hours. a,a'-dichloro-p-xylene (5 mmol) was added to the residue. The resulting solution was stirred at room temperature for another 4 hours. The solvent was removed under vacuum. The product was extracted with dichloromethane (DCM), and A was obtained in quantitative yield after removing the solvent. $^1$H NMR (CDCl$_3$): δ 7.55 (s, 2H), 7.13 (s, 4H), 7.10 (s, 2H), 6.89 (s, 2H), 5.12 (s, 4H). MS (GC-MS) m/z 238 (M$^+$).

For B, a,a'-dichloro-σ-xylene was used in the reaction instead of a,a'-dichloro-p-xylene. $^1$H NMR (CDCl$_3$): δ 7.45 (s, 2H), 7.38 (d, 2H), 7.12 (s, 2H), 7.08 (d, 2H), 6.80 (s, 2H), 5.03 (s, 4H). MS (GC-MS) m/z 238 (M$^+$).

For C, a DMF solution of benzyl chloride (252 mg, 2 mmol) was introduced to the DMF solution of A (714 mg, 3 mmol). The resulting solution was stirred at 90° C. for 8 hours. The solvent was removed under vacuum. The product was purified through flash column chromatography. $^1$H NMR (CDCl$_3$): δ 10.70 (s, 1H), 7.53 (m, 3H), 7.45 (m, 2H), 7.39 (m, 1H), 7.35 (m, 3H), 7.17 (m, 1H), 7.13 (d, 2H), 7.03 (s, 1H), 6.89 (s, 1H), 5.59 (s, 2H), 5.52 (s, 2H), 5.11 (s, 2H).

For D, B (238 mg, 1 mmol) was added to a DMF solution of a,a'-dichloro-p-xylene (5 mmol). The resulting solution was stirred at 90° C. for 8 hours. The reaction mixture was cooled down and filtered to remove the insoluble component. The solvent was removed under vacuum. Product D was purified by crystallization. $^1$H NMR (CD$_3$OD): δ 7.35-7.70 (m, 18H), 5.68 (s, 4H), 5.52 (s, 4H), 5.43 (s, 4H).

Figure 3:
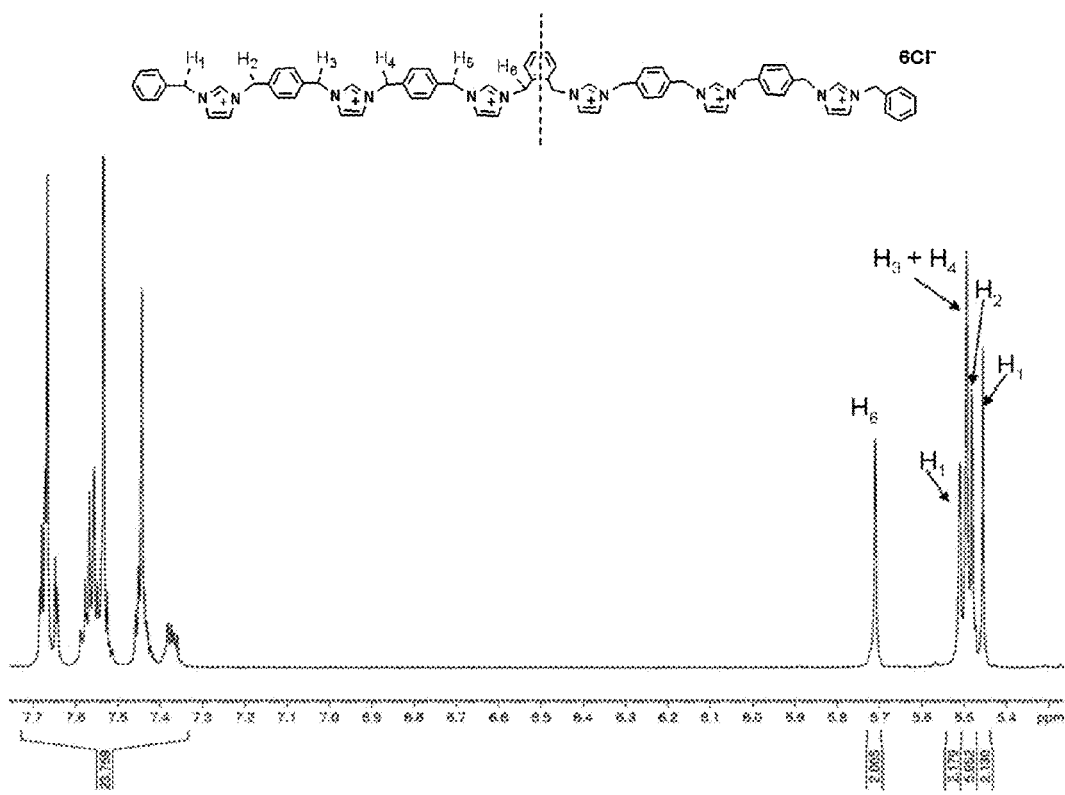
FIG. 3 depicts the NMR spectrum and structure of IBN-1.

For IBN-1, C (364 mg, 1 mmol) was added to a DMF solution of D (294, 0.5 mmol). The resulting solution was stirred at 90° C. for 8 hours. The solution part of reaction mixture was decanted, and the solid precipitation was washed by DMF and recrystallized from methanol solution to give IBN-1 in 90% yield. The NMR spectra of IBN-1 is shown in FIG. 3. $^1$H NMR (CD$_3$OD): δ 7.35-7.70 (m, 48H), 5.72 (s, 4H), 5.51 (s, 4H), 5.49 (s, 8H), 5.47 (s, 4H), 5.45 (s, 4H). MALDI-TOF-MS: m/z 185 (M$^{6+}$+1). Elemental analysis: C, 61.02; H, 6.05; N, 11.56; calc. for IBN-1 (5H$_2$O): C, 60.63; H, 5.94; N, 11.78.

Example 2

Synthesis of PIM-45

Figure 4:
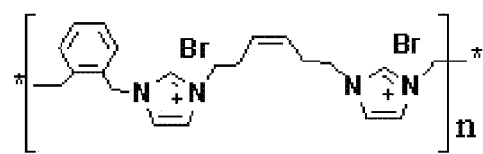
FIG. 4 depicts a molecular structure of PIM-45.
Figure 5A:
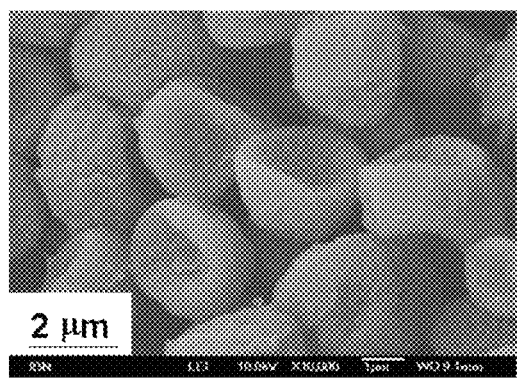
FIG. 5a depicts a SEM micrograph of the saline control having morphological changes in *A. niger* after incubation for 2 hours without IBN-1.
Figure 5B:
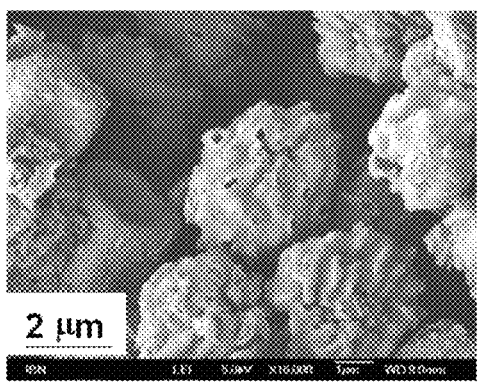
FIG. 5b depicts a SEM micrograph showing the morphological changes of *A. niger* after incubation for 2 hours with 62.5 μg/mL of IBN-1.
Figure 5C:
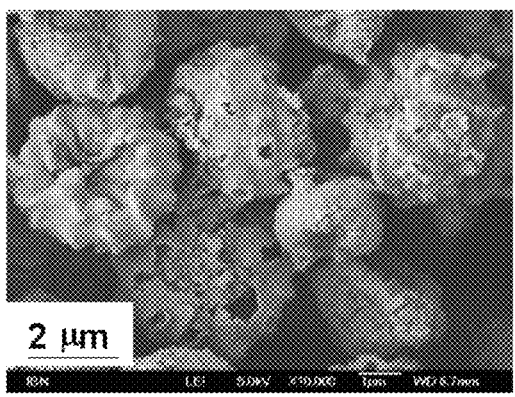
FIG. 5c depicts a SEM micrograph showing the morphological changes of *A. niger* after incubation for 2 hours with 125 μg/mL of IBN-1.
Figure 5D:
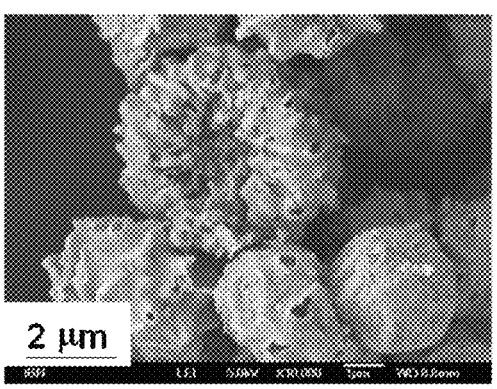
FIG. 5d depicts a SEM micrograph showing the morphological changes of *A. niger* after incubation for 2 hours with 250 μg/mL of IBN-1.
Figure 5E:
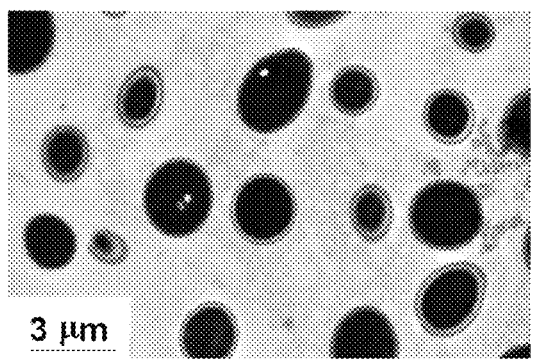
FIG. 5e depicts a TEM micrograph of the saline control having morphological changes in *C. albicans* after incubation for 2 hours without PIM-45.
Figure 5F:
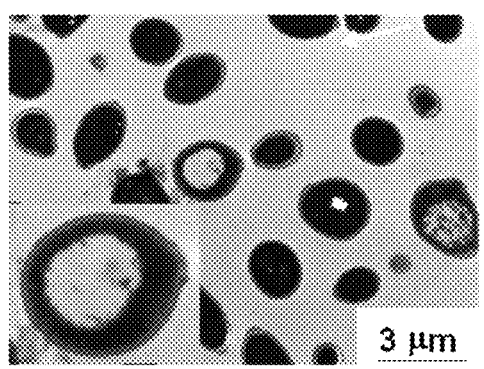
FIG. 5f depicts a TEM micrograph showing the morphological changes of lytic cells of *C. albicans* after incubation for 2 hours with 32.5 μg/mL of PIM-45 (2×MIC).
Figure 5G:
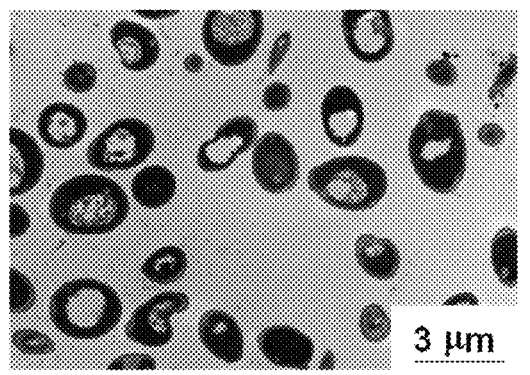
FIG. 5g depicts a TEM micrograph showing the morphological changes of lytic cells of *C. albicans* after incubation for 2 hours with 156 μg/mL of PIM-45 (10×MIC).
Figure 5H:
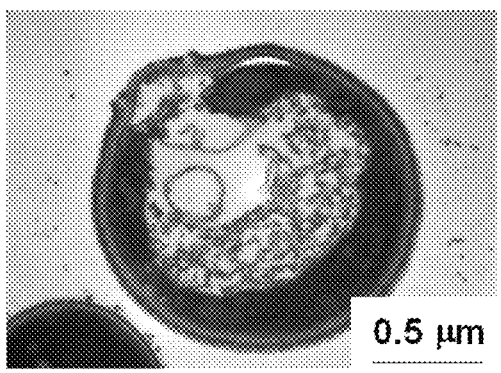
FIG. 5h depicts a TEM micrograph showing the disintegrated cell walls of the lytic cells of *C. albicans* after incubation for 2 hours with 156 μg/mL of PIM-45 (10× MIC).

Main-chain polyimidazolium PIM-45 was prepared from the condensation reaction intermediate B (see FIG. 2) with 1,4-dibromobutylene in tetrahydrofuran (THF). B (238 mg, 1 mmol) was added to a THF solution (10 mL) of 1,4-dibromobutylene (214 mg, 1 mmol). The resulting solution was stirred at 90° C. for 4 hours. The reaction mixture was cooled, and filtered to remove the liquid component. The solid was washed with DMF and with THF, and then dried under vacuum. PIM-45 was produced as a white powder. $^1$H NMR (CD$_3$OD): δ 7.35-7.70 (m, 18H), 5.68 (s, 4H), 5.52 (s, 4H), 5.43 (s, 4H). Mw=2869 and PDI=1.03. The molecular structure of PIM-45 is shown in FIG. 4.

Results and Discussion

PIMSs were synthesized based on condensation reactions as reported in examples 1 and 2 above. After screening various linker groups, two leading compounds, IBN-1 and PIM-45, were selected for detailed studies. IBN-1 is an oligomer with 6 imidazolium units in the structure ($C_{72}H_{72}N_{12}Cl_6$, Mw=1316) (see FIG. 3). PIM-45 is a polymer with an average molecular weight (Mn) of 2781 by gel permeation chromatography (GPC) (Mw/Mn=1.03) (see FIG. 4).

The in vitro antifungi properties of these two compounds were tested on planktonic yeast-like fungi C. albicans and filamentous fungi A. niger. In vitro fungicidal studies indicated that the MICs against C. albicans and A. niger were 31.2 ppm of IBN-1 for both, and 15.6 ppm and 125 ppm of PIM-45, respectively (see FIG. 11a to 11d). As a comparison, MICs against CA were obtained for amphotericin B (3.9 ppm) and fluconazole (>125 ppm). PIMSs showed a lower in vitro potency than amphotericin B, but a higher in vitro potency than fluconazole. Unlike amphotericin B and fluconazole, the stability of the PIMSs could be maintained in PBS. PIMSs were kept in PBS at room temperature for 6 months without any protection from light. Sterility tests were then performed, and the results indicated that the PIMSs were chemically stable in the solution since the microbiological activity of the solution was preserved. After treatment with PIMSs, the fungi showed empty cytoplasms with completely damaged cell walls. FESEM images show that the smooth surface of the A. niger cells became swollen, deformed and porous after 2 hours exposure to IBN-1 (FIGS. 5a to 5d). Cell wall alterations were also evident in the PIM-45-treated C. albicans (see FIGS. 5e to 5h). These morphological changes suggested that main-chain PIMSs possessed potent biocidal activities, causing the leakage of cytoplasm by making the cell membrane porous. In addition, both IBN-1 and PIM-45 gave rise to very little hemolysis of only ~1% even at a concentration of 5000 μg/mL. This illustrated that PIMSs have significantly improved selectivity as compared to simple imidazolium salts and other synthetic macromolecules.

Figure 6:
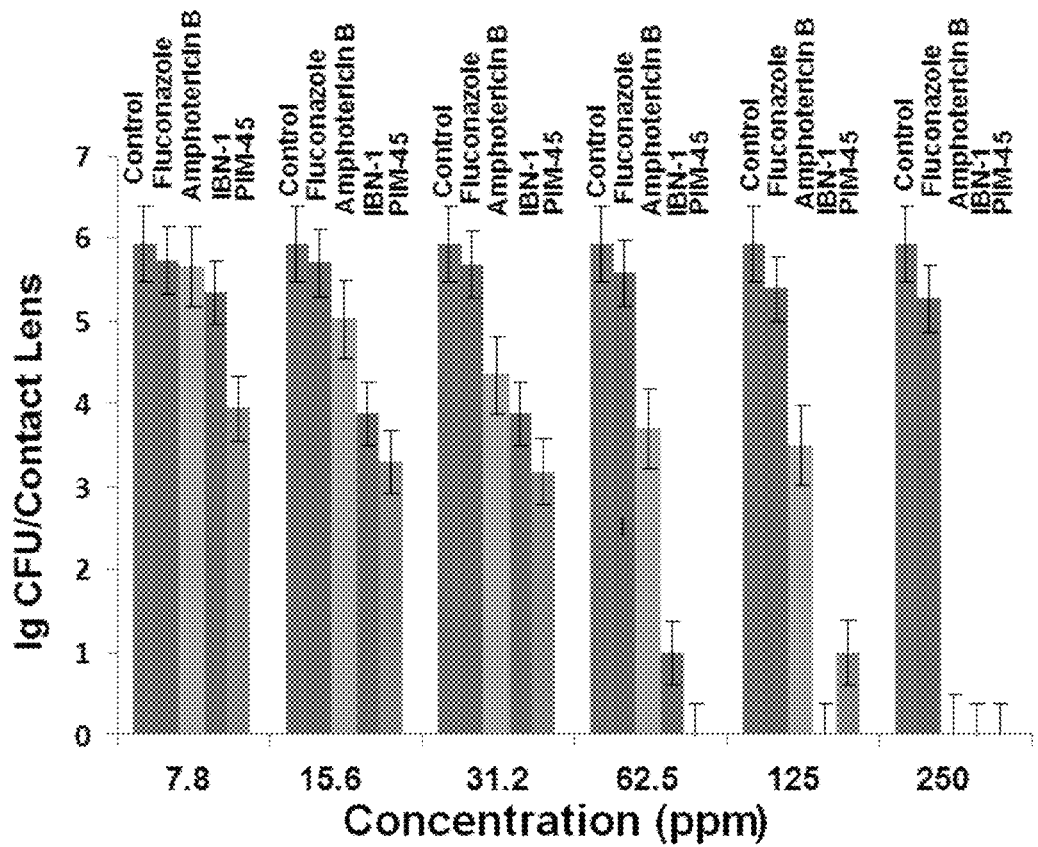
FIG. 6 shows the dose-dependent susceptibility of contact lens-supported *C. albicans* biofilms against fluconazole, amphotericin B, IBN-1 and PIM-45 in PBS. Data points represent the mean colony counts calculated from three separate experiments.

In vitro C. albicans keratitis (biofilm) treatments were conducted with IBN-1, PIM-45, amphotericin B and fluconazole. FIG. 6 shows that fluconazole only slightly destroyed the C. albicans biofilm at 250 ppm. Although amphotericin B inhibited the growth of planktonic C. albicans at concentrations below 4 ppm, the activity in killing the adhered cells on contact lens (biofilm) was low, requiring an effective concentration of 250 ppm. In contrast, the effective concentration of short imidazolium polymer (PIM-45) and oligomer (IBN-1) in killing biofilm-grown yeast cells was ~4-fold lower (i.e. ~62.5 ppm for both compounds). This could be attributed to the excellent penetration characteristics of PIMSs as compared to amphotericin B.

Figure 7A:
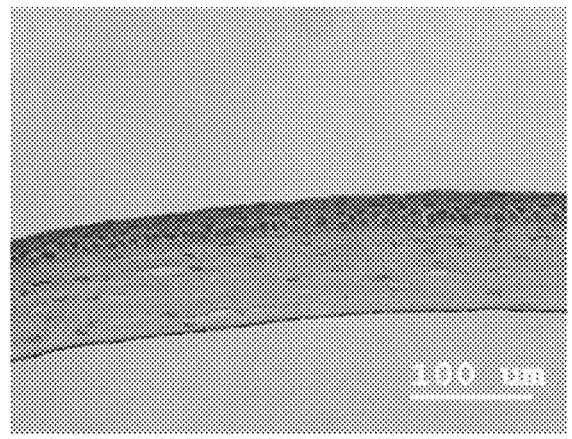
FIG. 7a depicts the histological sections of a mouse cornea with hematoxycin and eosin after topical administration of 1000 ppm of PIM-45 in an in vivo biocompatibility studies. Scale bar represents 100 um.
Figure 7B:
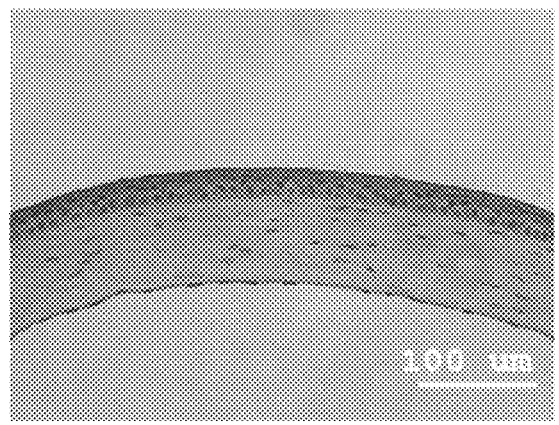
FIG. 7b depicts the histological sections of a mouse cornea with hematoxycin and eosin after topical administration of 1000 ppm of IBN-1 in an in vivo biocompatibility studies. Scale bar represents 100 um.
Figure 7C:
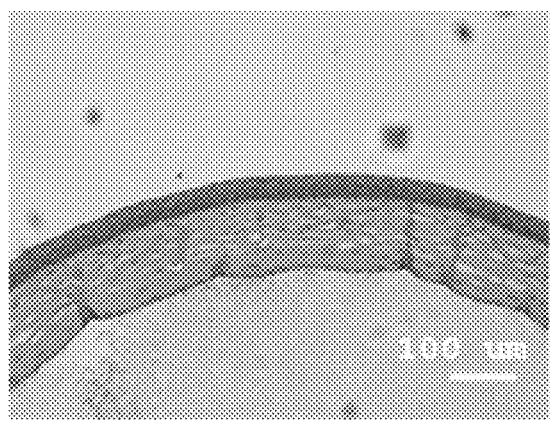
FIG. 7c depicts the histological sections of a mouse cornea with hematoxycin and eosin used as a saline control in an in vivo biocompatibility studies. Scale bar represents 100 um.
Figure 8A:
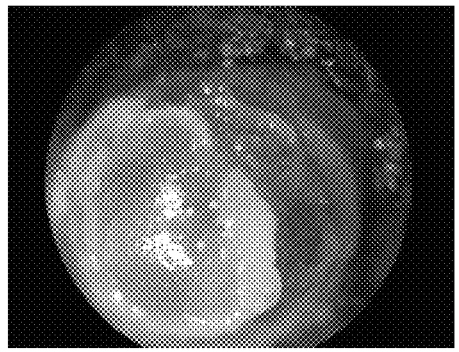
FIG. 8a depicts a mouse eye with *C. albicans* used as a control after treatment with saline.
Figure 8B:
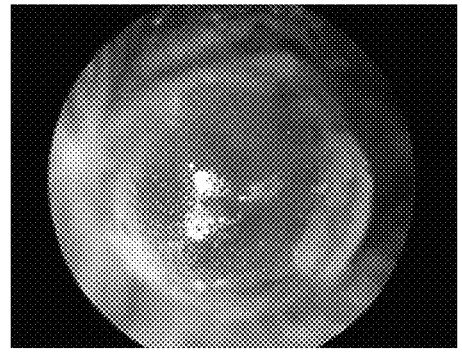
FIG. 8b depicts a mouse eye with *C. albicans* used as a control after treatment with amphotericin B.
Figure 8C:
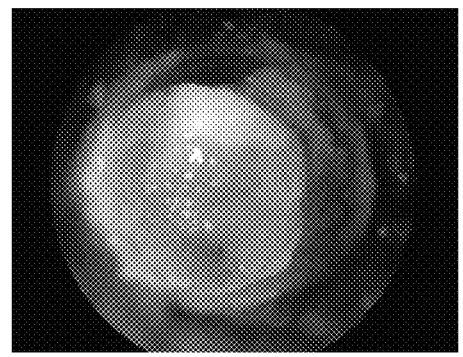
FIG. 8c depicts a mouse eye with *C. albicans* used as a control after treatment with fluconazole.
Figure 8D:
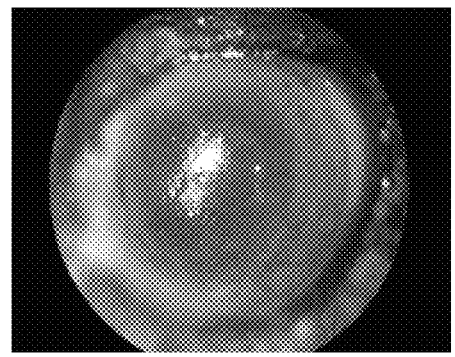
FIG. 8d depicts a mouse eye with *C. albicans* used as a control after treatment with PIM-45.
Figure 8E:
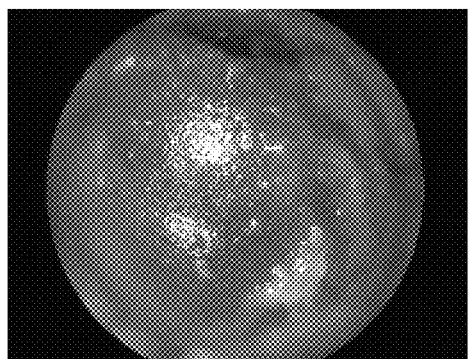
FIG. 8e depicts a mouse eye with *C. albicans* used as a control after treatment with IBN-1.
Figure 9A:
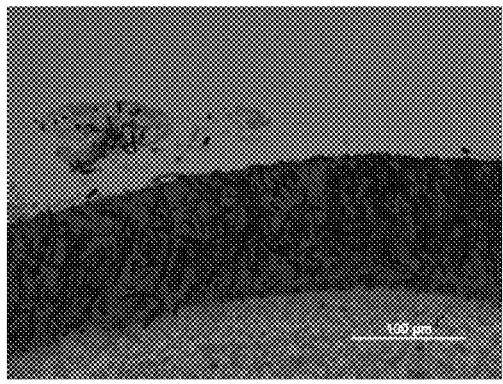
FIG. 9a depicts the histology of a mouse cornea treated with saline.
Figure 9B:
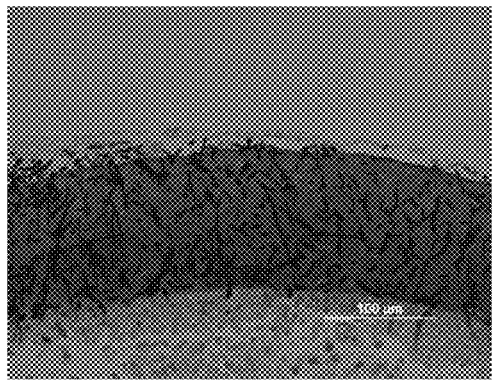
FIG. 9b depicts the histology of a mouse cornea treated with fluconazole.
Figure 9C:
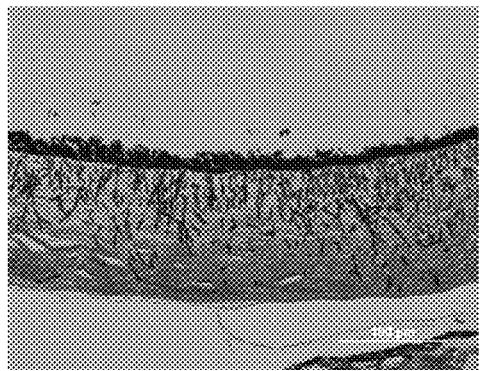
FIG. 9c depicts the histology of a mouse cornea treated with amphotericin B.
Figure 9D:
FIG. 9d depicts the histology of a mouse cornea treated with PIM-45.
Figure 9E:
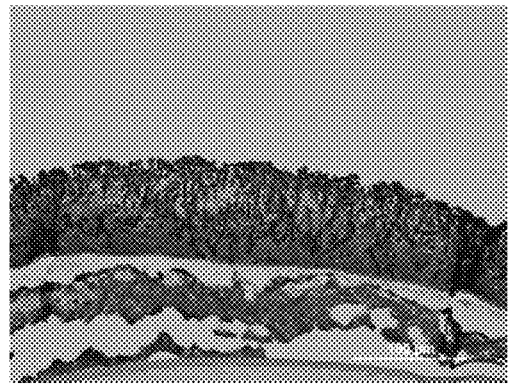
FIG. 9e depicts the histology of a mouse cornea treated with IBN-1.
Figure 12A:
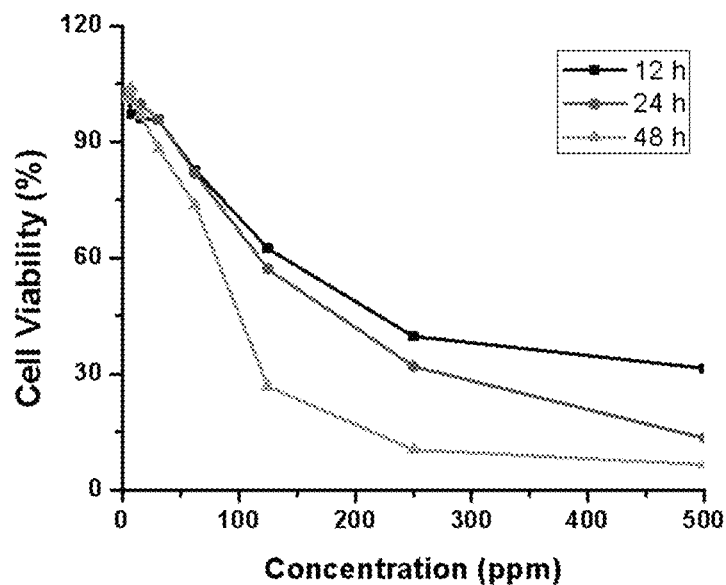
FIG. 12a shows the result of in vitro biocompatibility test of PIM-45 by incubation with HCEP cells.
Figure 12B:
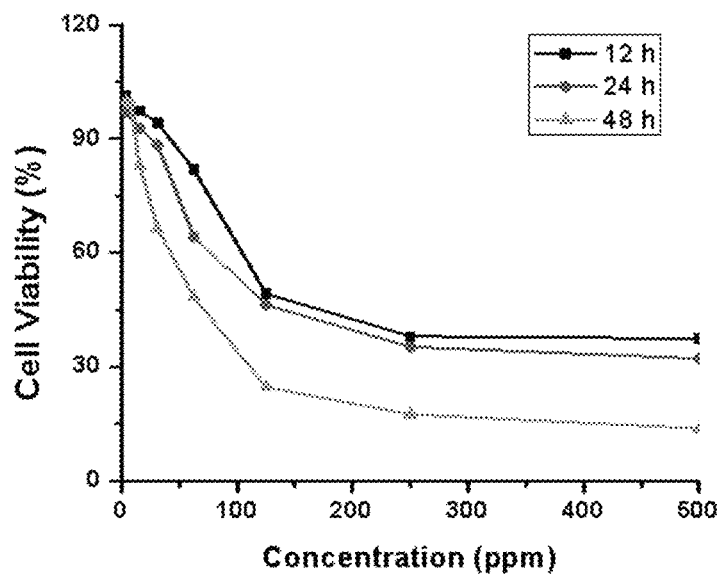
FIG. 12b shows the result of in vitro biocompatibility test of IBN-1 by incubation with HCEP cells.

The biocompatibility and toxicity of PIMSs were tested in both in vitro and in vivo models. The in vitro biocompatibility of PIM-45 and IBN-1 was evaluated by incubation with HCEP cells. ~90% of the cells were still alive after 12 hours of incubation with 62.5 ppm of the PIMSs (FIGS. 12a and 12b). PIM-45 (1000 ppm) and IBN-1 (1000 ppm) was selected for in vivo toxicity study. Histological images of the cornea after topical administration of PIM-45 and IBN-1 did not show significant signs of corneal epithelial erosion (FIGS. 7a to 7c). PIM-45 and IBN-1 solution did not lead to obvious pathological changes of the underlying stroma.

PIM-45 and IBN-1 demonstrated high potency against both planktonic fungi and biofilm, as well as excellent biocompatibility. To investigate the potential application of these two compounds in fungi keratitis treatment, C. albicans keratitis model was established using mouse. The contact lenses with C. albicans biofilm were kept inside the mice eyes by closing the lids with silk sutures. 18 hours after inoculation, the C. albicans cells were grown on the eyeball. Eye ulcer with a leathery, tough, raised surface was observed. The animals were randomly treated with 5 topical eye drop solutions: saline solution (control), 1000 μg/mL of PIM-45, 1000 μg/mL of IBN-1, 1000 μg/mL of amphotericin B, and 1000 μg/mL of fluconazole. Eye drops (20 μl each)

were administered to the mice every minutes during the first hour and every 30 minutes during the next 7 hours. After a pause of 16 hours, eye drops were administered at hourly intervals for another 8 hours. All mice were sacrificed 16 hours after the administration of the last eye drop. The treated eyeballs were collected immediately; three eyeballs from each group were collected for histology, and the remaining 6 eyeballs were homogenized for quantitative fungal recovery study. The fixed eyeballs were embedded in paraffin, sectioned and stained with Grocott's methenamine silver by standard protocol.

Figure 10:
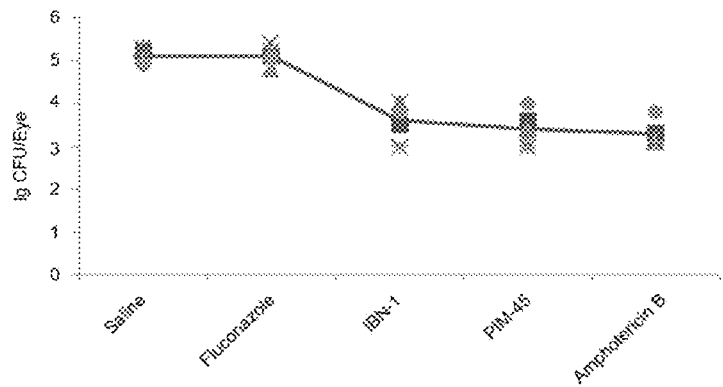
FIG. 10 shows the microbiology counts of *C. albicans* from six mice cornea samples for each individual treatment with saline, fluconazole, IBN-1, PIM-45 and amphotericin B. The line represents the average value.
Figure 11A:
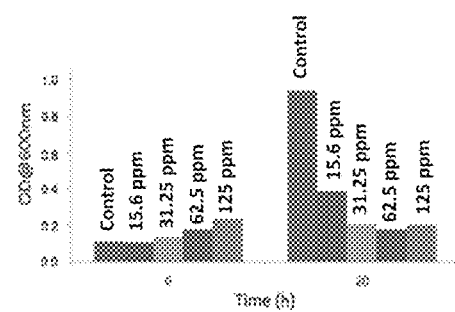
FIG. 11a depicts the MIC test results of PIM-45 against planktonic *C. albicans*.
Figure 11B:
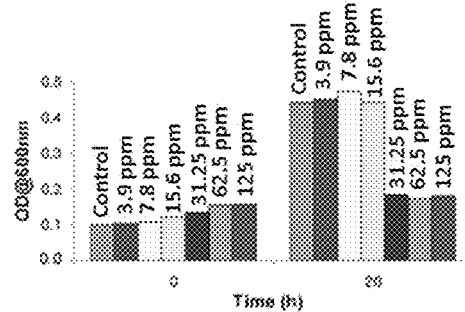
FIG. 11b depicts the MIC test results of IBN-1 against planktonic *C. albicans*.
Figure 11C:
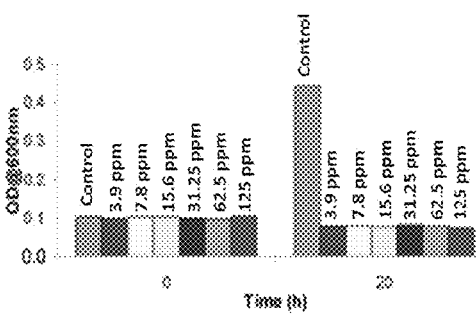
FIG. 11c depicts the MIC test results of amphotericin B against planktonic *C. albicans*.
Figure 11D:
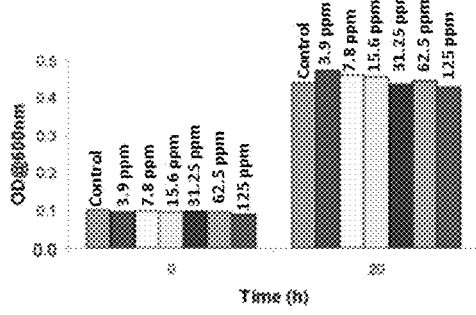
FIG. 11d depicts the MIC test results of fluconazole against planktonic *C. albicans*.
Figure 13:
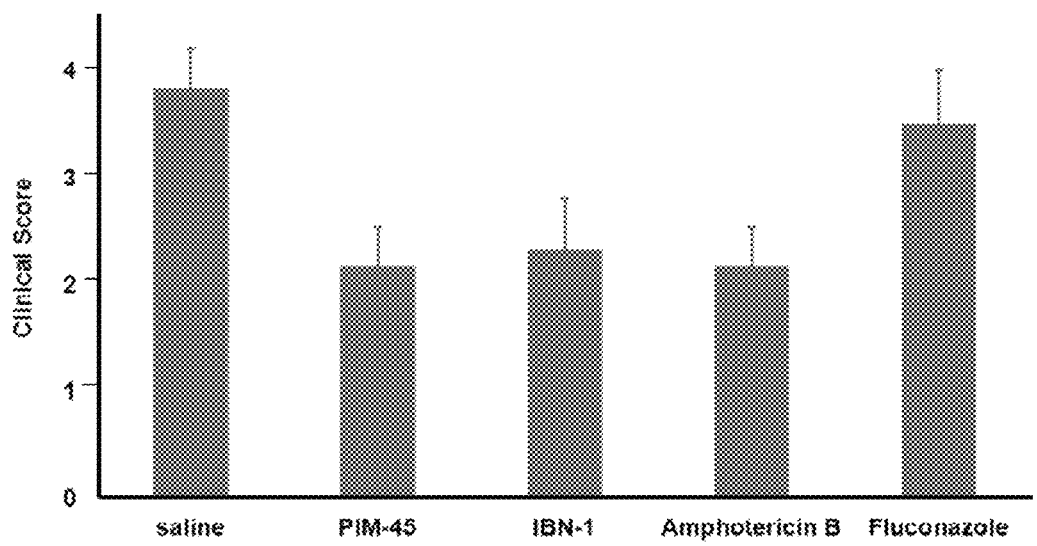
FIG. 13 shows the clinical slit lamp scores (±standard deviation) for keratitis before and after treatment with five topical eye drops solutions comprising saline (control), PIM-45, IBN-1, amphotericin B and fluconazole.

For the eyes treated with saline and fluconazole, fungal hyphae extended through the epithelium and into the anterior stroma, which was associated with intense leukocyte infiltration in the cornea and anterior chamber. In contrast, amphotericin B, PIM-45 and IBN-1 reduced the maximal depth of hyphal invasion into cornea (FIGS. 8a to 8e and 9a to 9e). Microbiology counts verified that treatments with PIM-45, IBN-1 and amphotericin B significantly decreased the corneal counts of C. albicans (3.4, 3.6, 3.3 lg CFU/eye), as compared to treatments with saline and fluconazole (5.2 and 5.1 lg CFU/eye) (FIG. 10). The clinical scores of PIM-45, IBN-1 and amphotericin B treated mice were 2.2±0.4, 2.3±0.5 and 2.2±0.4 respectively, which were significantly lower than that of the saline and fluconazole treated mice (3.8±0.4 and 3.5±0.5, respectively) (FIG. 13 and Table 1 above).

Based on the above results, main-chain imidazolium polymer PIM-45 and oligomer IBN-1 effectively inhibited growth of fungi with low MIC values, and successfully cleared the fungal biofilm. Compared to the costly and unstable amphotericin B and fluconazole solutions, PIM-45 and IBN-1 solutions are easy to prepare and can be stored in PBS for routine topical use with long shelf life. Preliminary keratitis treatment studies indicated that the topical solution of PIMSs were safe and as efficacious as that of amphotericin B, the most commonly used agent for the treatment of C. albicans keratitis.

Applications

The disclosed antimicrobial and/or antifungal drugs may be used as an effective therapy for fungal infections such as eye diseases, in particular fungal keratitis.

The disclosed antimicrobial and/or antifungal drugs may also be used in the manufacture of a medicament for the treatment of a fungal infection such as an eye disease, in particular fungal keratitis.

The disclosed drugs may be used to treat any form of fungi growth or infection that forms a keratinous substrate or film which impairs eyesight. These fungi may include yeast-like fungi such as C. albicans or filamentous fungi such as Aspergillus fumigatus and A. niger.

The disclosed drugs may exhibit good penetration, solubility, long term storage stability with improved selectivity and MHC/MIC.

The disclosed drugs may not require a high dosage and may be a broad-spectrum efficient drug. Thus, the disclosed drugs serve as a cost effective means for the treatment of a fungal infection such as fungal keratitis.

The disclosed drug may be further used in the pharmaceutical industries as it may possess biological characteristics such as being anti-oxidative, anti-inflammatory, anti-fibrotic and anti-cancer.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of treating or preventing a fungal infection caused by *Aspergillus niger*, comprising the step of administering an antifungal amount of a compound to a patient in need thereof, said compound having the general formula (I):

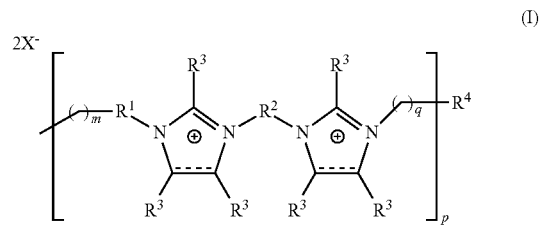

wherein:

$R^1$ and $R^2$ are each independently selected from aryl, arylalkyl, alkylarylalkyl, alkylaryl, alkyl, cycloalkyl, alkenyl or alkynyl, said aryl, arylalkyl, alkylarylalkyl or alkylaryl being optionally substituted by alkyl, alkenyl or alkynyl;

each $R^3$ is independently selected from hydrogen, alkyl, alkenyl, alkynyl, aryl, cycloalkyl, heteroaryl, or heterocyclyl;

$R^4$ is selected from hydrogen or aryl, said aryl being optionally substituted by alkyl, alkenyl or alkynyl;

˗˗˗˗˗˗ is either a single bond or a double bond;

q is an integer selected from 0 to 3;

m is an integer selected from 0 to 3;

p is an integer selected from 2 to 50; and $X^-$ is a counterion.

2. The method according to claim 1, wherein $R^1$ or $R^2$ are independently selected from aryl, arylalkyl or alkylarylalkyl.

3. The method according to claim 1, wherein $R^1$ or $R^2$ are independently selected from phenyl, phenylmethyl or methylphenylmethyl.

4. The method according to claim 3, wherein said phenyl, phenylmethyl or methylphenylmethyl is substituted at the ortho position or at the meta position.

5. The method according to claim 1, wherein $R^2$ is selected from $C_{1-6}$-alkyl or $C_{2-6}$-alkenyl.

6. The method according to claim 5, wherein $R^2$ is selected from the group consisting of methyl, ethyl, propyl, butyl, pentyl, hexyl, ethylene, propylene, butylene, pentylene or hexylene.

7. The method according to claim 6, wherein said hexylene is 3-hexenyl.

8. The method according to claim 1, wherein $R^3$ is selected from hydrogen.

9. The method according to claim 1, wherein $R^4$ is hydrogen or phenyl.

10. The method according to claim 1, wherein X is a halide selected from the group consisting of fluoride, iodide, bromide and chloride.

11. The method according to claim 1, wherein said compound of formula (I) has a molecular weight in the range of 1000 to 3000.

12. The method according to claim 1, wherein a compound of formula (I) is selected from formula (II) or formula (III):

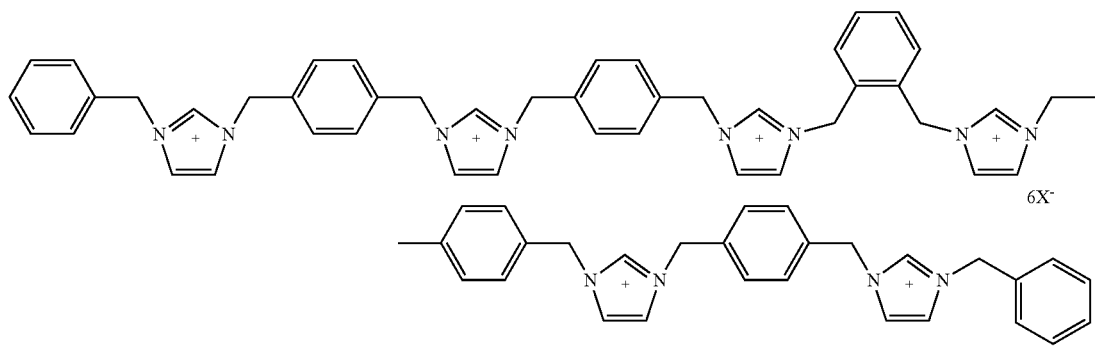

Formula (II)

Formula (III)

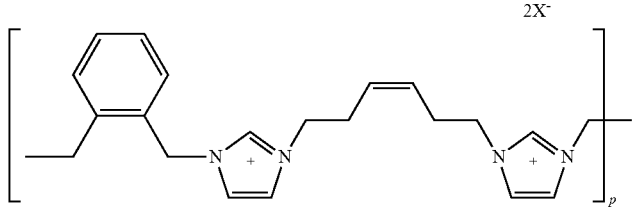

wherein p is 6 to 20.

13. The method according to claim 1 wherein said fungal infection is selected from keratitis or aspergillosis.

14. A method of reducing the fungal cell count on a fungal biofilm, comprising the step of administering an effective fungicidal amount of a compound selected to confer the fungicidal effect, said compound having the general formula (I):

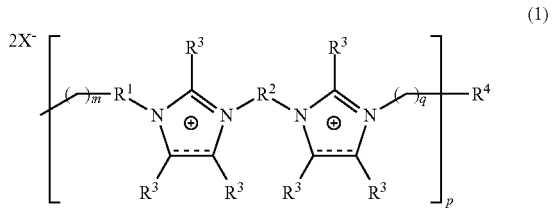

wherein:

$R^1$ and $R^2$ are each independently selected from aryl, arylalkyl, alkylarylalkyl, alkylaryl, alkyl, cycloalkyl, alkenyl or alkynyl, said aryl, arylalkyl, alkylarylalkyl or alkylaryl being optionally substituted by alkyl, alkenyl or alkynyl;

each $R^3$ is independently selected from hydrogen, alkyl, alkenyl, alkynyl, aryl, cycloalkyl, heteroaryl, or heterocyclyl;

$R^4$ is selected from hydrogen or aryl, said aryl being optionally substituted by alkyl, alkenyl or alkynyl;

------ is either a single bond or a double bond;

q is an integer selected from 0 to 3;

m is an integer selected from 0 to 3;

p is an integer selected from 2 to 50; and $X^-$ is a counterion.

* * * * *